(12) United States Patent
Bock

(10) Patent No.: US 6,490,479 B2
(45) Date of Patent: Dec. 3, 2002

(54) ATRIAL FIBRILLATION DETECTION METHOD AND APPARATUS

(75) Inventor: Elizabeth Anne Bock, Elm Grove, WI (US)

(73) Assignee: GE Medical Systems Information Technologies, Inc., Milwaukee, WI (US)

(*) Notice: Subject to any disclaimer, the term of this patent is extended or adjusted under 35 U.S.C. 154(b) by 124 days.

(21) Appl. No.: 09/750,846

(22) Filed: Dec. 28, 2000

(65) Prior Publication Data

US 2002/0143266 A1 Oct. 3, 2002

(51) Int. Cl.[7] .............................................. A61B 5/0468
(52) U.S. Cl. ........................................ 600/518; 600/512
(58) Field of Search ................................... 600/518, 512

(56) References Cited

U.S. PATENT DOCUMENTS

| | | | | |
|---|---|---|---|---|
| 5,423,863 A | * | 6/1995 | Felblinger et al. | 600/518 |
| 5,456,261 A | * | 10/1995 | Luczyk | 600/518 |
| 5,840,038 A | | 11/1998 | Xue et al. | |
| 6,178,347 B1 | * | 1/2001 | Olsson | 600/518 |
| 6,226,599 B1 | * | 5/2001 | Deco et al. | 600/518 |
| 6,269,263 B1 | * | 7/2001 | Ohnishi et al. | 600/518 |

* cited by examiner

Primary Examiner—Paul J. Hirsch
(74) Attorney, Agent, or Firm—Michael Best & Friedrich LLP

(57) ABSTRACT

A method and apparatus to detect irregular heart activity based upon a ventricular activity analysis, P wave activity, similarities in R wave to R wave intervals, and a state evaluation. The invention includes a beat classification module that receives ECG information as an input. The beat classification module determines whether the heart beat being analyzed falls within classifications that are suitable for use in analyzing whether an irregular condition exists. If the beat falls within a class suitable for analysis, the ECG information is fed to an interval calculator. The interval calculator determines the interval between successive R waves. The information from the interval calculator is provided to a probability engine and to a contextual analysis module. The probability engine is designed to detect atrial fibrillation based upon beat classification and RR interval values from the interval calculator. The probability engine outputs a state variable that indicates a probability of whether an irregular condition is present. The contextual analysis module matches predefined maps to a running map of the current ECG information. The contextual analysis module also determines the similarity between consecutive RR intervals and checks for sequences of matching classes. ECG information is also supplied to a P wave detection module to detect the presence of P waves. Information from the probability analysis engine, the contextual analysis module, and the P wave detection module is then provided to a state evaluation module. The state evaluation module uses the outputs of the three modules to determine whether an irregular condition exists.

34 Claims, 7 Drawing Sheets

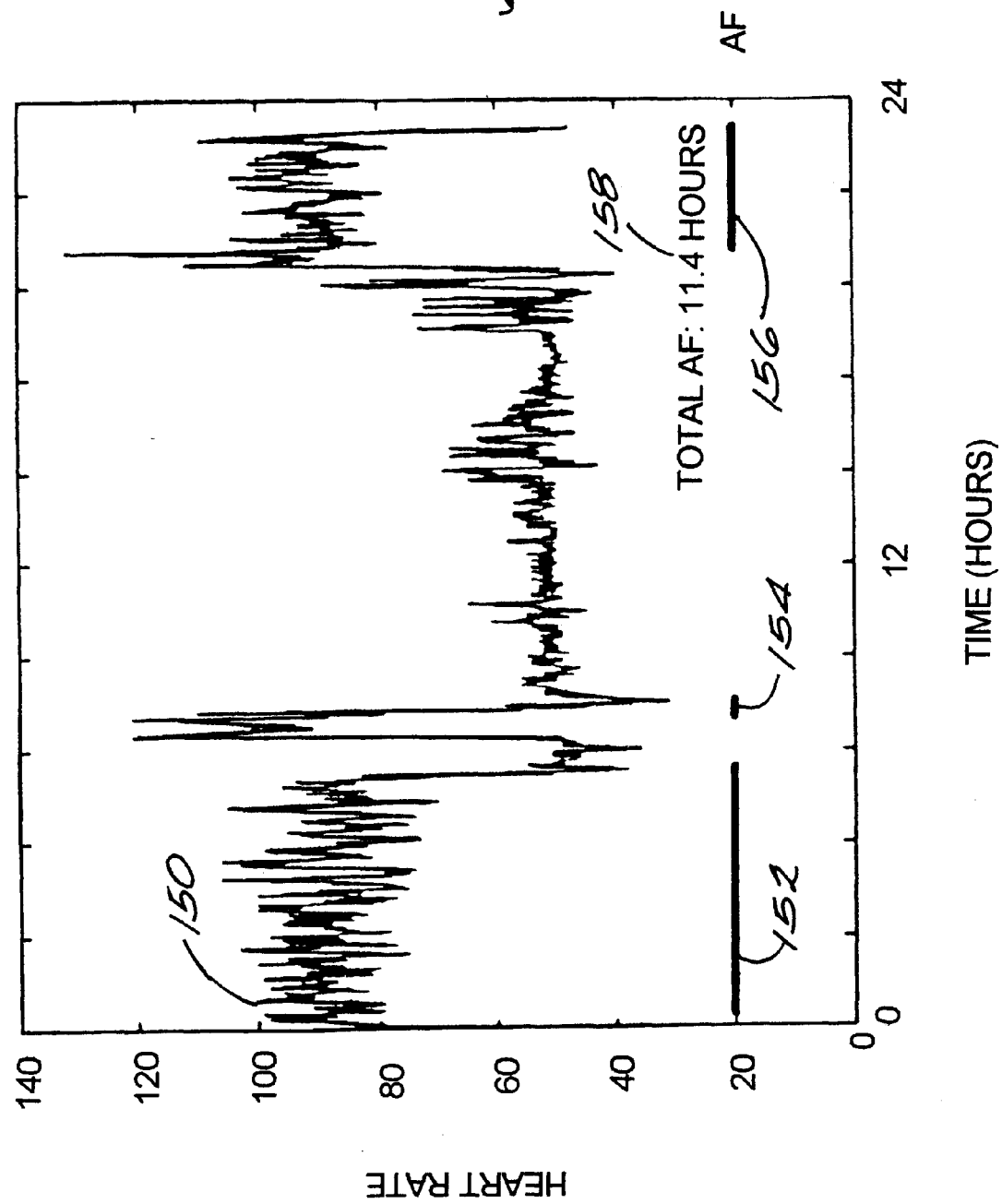

ATRIAL FIBRILLATION DETECTION METHOD AND APPARATUS

BACKGROUND OF THE INVENTION

The present invention relates to methods and devices used to detect irregularities in the beating of an animal heart, generally known as "arrhythmias." More particularly, the invention relates to a method and an apparatus to detect atrial fibrillation ("AF").

As is well known in the medical field, the contraction of an animal heart is controlled by a series of electrical signals that originate in the sinus node of the right atrium. These signals can be recorded and the record can be used as a diagnostic and treatment tool. An electrocardiogram ("ECG") is a graphic display of the electrical signals that cause the heart to contract. A representative ECG waveform 10 is shown in FIG. 1. The ECG 10 includes a number of crests (generally referred to as "waves") and a number of troughs. A normal ECG, such as the ECG waveform 10, includes a P wave, which represents the electrical potential generated as atrial cells in the heart depolarize before contraction. Following the P wave is a crest and trough combination known as the QRS complex, which includes Q, R, and S waves. The QRS complex is caused by the electrical potential generated when the ventricular muscle cells depolarize before contraction. Following the QRS complex is a T wave. The T wave is caused by electrical potential generated as the ventricles of the heart recover from the state of the polarization. Following the T wave is a short period of relative inactivity. A new contraction begins with a second P wave, $P_2$.

A variety of methods and devices have been developed to assist physicians in interpreting ECGs. One such tool is known as EKpro detection software, which is available from GE Medical Systems Information Technologies, Inc., the assignee of the present application. EKpro software is designed for monitoring ECG signals in adults and paced patients. EKpro software has particular application in detecting atrial fibrillation. AF is identified by an irregular heart rhythm and is clinically defined as uncoordinated contractions of the atria. The ECG of a patient suffering from atrial fibrillation typically demonstrates irregular ventricular contractions and the absence of P waves. If allowed to continue, AF can cause decreases in exercise tolerance and left ventricular function. In more severe cases, AF can lead to a fatal medical condition.

The problems associated with AF can be reversed if sinus rhythm can be restored. The identification of AF allows a caregiver to administer a treatment to control symptoms and to prevent more serious complications. Most often, the treatment is specific to the nature of the atrial fibrillation suffered by the patient and, in particular, the heart rate of the patient, the symptoms suffered by the patient, and the duration of the AF events. Some current software systems attempt to detect AF based on ventricular activity. However, these types of systems can, in general, only suggest that an irregular rhythm may be caused by atrial fibrillation. One version of the EKpro product mentioned above is used in Holter monitoring, and determines the probability of an AF condition using a Hidden Markov Model ("HMM") methodology. While the EKpro product is better than many others in predicting an AF condition, it still suffers from the problem of relying solely on ventricular data, and is dependent upon the data used to train it. In order to provide accurate predictions a complete data set covering all irregular heart rhythms, not just AF, is required. Since such data sets are often difficult to compile, a system solely dependent on a HMM methodology can be biased.

Another difficulty with present systems is that many are not, in general, able to specifically identify AF over other irregular rhythms. The inability to specifically identify the exact irregular rhythm suffered by the patient is problematic in hospital environments, where most patient monitoring is alarm-based. That is, whenever any irregular condition is detected, an alarm is set off. When an alarm sounds, a medical professional must respond. The medical professional can assess the situation and identify if the alarm is true or false. If there are too many false alarms, the medical professional may become desensitized, responding slowly or lackadaisically to alarms. This may cause a professional to respond inadequately when a severe or critical condition occurs.

SUMMARY OF THE INVENTION

Accordingly, it would be desirable to have an improved method and device to detect AF. In addition, since atrial fibrillation is typically not a life-threatening arrhythmia, an alternative solution to alarm-based monitoring system would be desirable so that medical professionals could respond in a manner that is proportionate to the significance of the irregular event, rather than treating all events equally.

The invention provides a method and apparatus that detects AF based upon a ventricular activity analysis, P wave activity, similarities in R wave to R wave intervals, and a state evaluation. In one embodiment, the invention includes a beat classification module that receives ECG information as an input. The beat classification module determines whether the heart beat being analyzed falls within classifications that are suitable for use in analyzing whether an AF condition exists. If the beat falls within a class suitable for analysis, the ECG information is fed to an interval calculator. The interval calculator determines the time interval between successive R waves (the "RR interval"). The information from the interval calculator is provided to a probability engine and to a contextual analysis module. The probability engine is designed to detect atrial fibrillation based upon beat classification and RR interval values from the interval calculator. The probability engine outputs a state variable that indicates whether an AF condition is present. The contextual analysis module matches predefined maps to the running map of the current ECG information. The contextual analysis module also determines the similarity between consecutive RR intervals. In addition, the classifications determined by the beat classification module are used by the contextual analysis module to check for sequences of matching classes. This analysis imposes a refractory period before the triggering of an alarm, in those circumstances where an AF condition exists.

ECG information is also supplied to a P-wave detection module. The P-wave detection module receives beat classification information from the beat classification module. In one embodiment of the invention, each beat shape is represented by a template, with the dominant shape of the ECG information being analyzed represented in a "favorite" template. When normal dominant beats are detected, they are used to incrementally update the favorite template. The favorite template is then used to determine whether P-waves are present in the dominant beat class. Information from the probability analysis engine, the contextual analysis module, and the P-wave detection module is then provided to a state evaluation module. The state evaluation module uses the outputs of the three noted modules to determine whether an atrial fibrillation condition exists. If the probability engine module outputs a state variable indicating an atrial fibrillation condition and the P-wave detection and contextual analysis modules output negative indicators, then an atrial fibrillation condition output is generated. However, before the state evaluation module outputs an alarm, the atrial fibrillation condition must exist for a specified amount of time. Likewise, a non-atrial fibrillation condition must exist for specified amount of time before an alarm is disabled.

The invention may also be embodied in a method. The method includes classifying ECG information, determining an interval between recurring events in the ECG information, determining the probability that an irregular condition exists based on classifying the ECG information and determining an interval between recurring events, and generating a state variable based on the determined probability. The state variable provides an indication of whether an irregular condition exists. In the invention, this indication is supplemented by generating a contextual output based on matching predefined maps to a current map of the ECG information, determining the presence of a P wave in the ECG information, and generating a detection output based on the presence of a P wave. The ultimate determination of whether the irregular condition exists is based on the state variable, the contextual output, and the detection output.

As is apparent from the above, it is an advantage of the present invention to provide an atrial fibrillation detection method and apparatus. Other features and advantages of the present invention will become apparent by consideration of the detailed description and accompanying drawings.

BRIEF DESCRIPTION OF THE DRAWINGS

In the drawings:

FIG. 7 is an illustration of atrial fibrillation data that may be generated with the invention.

DETAILED DESCRIPTION

Figure 1:
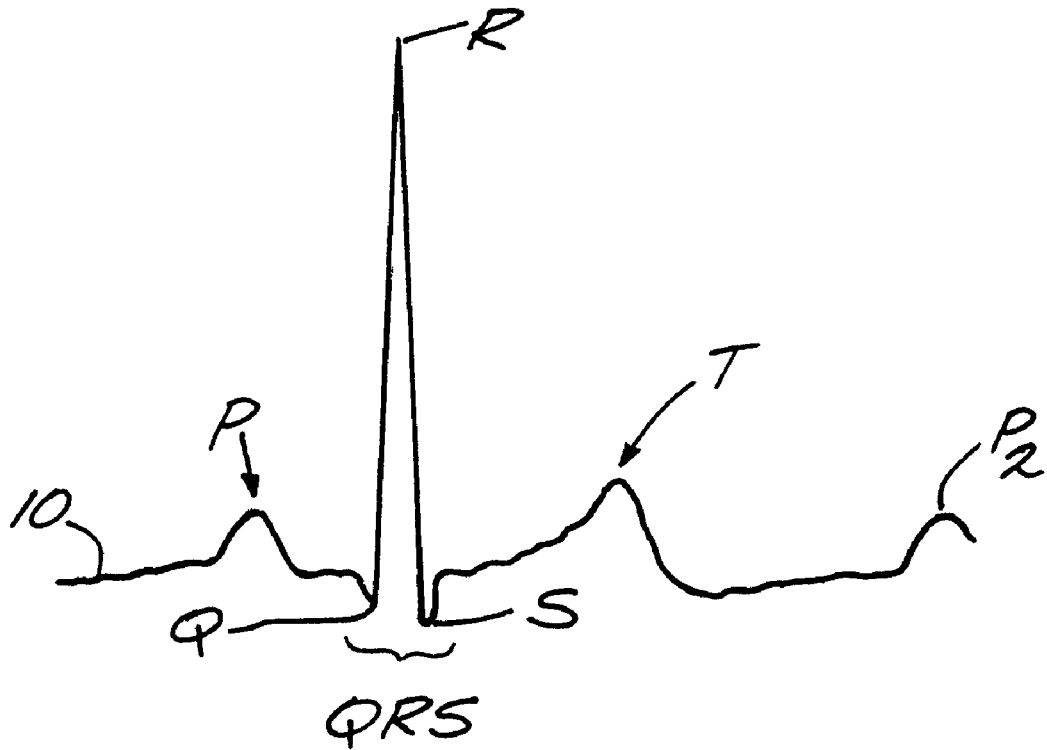
FIG. 1 is an illustration of a typical ECG waveform in a healthy patient.

Before one embodiment of the invention is explained in detail, it is to be understood that the invention is not limited in its application to the details of the construction and the arrangements of the components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

Figure 2:
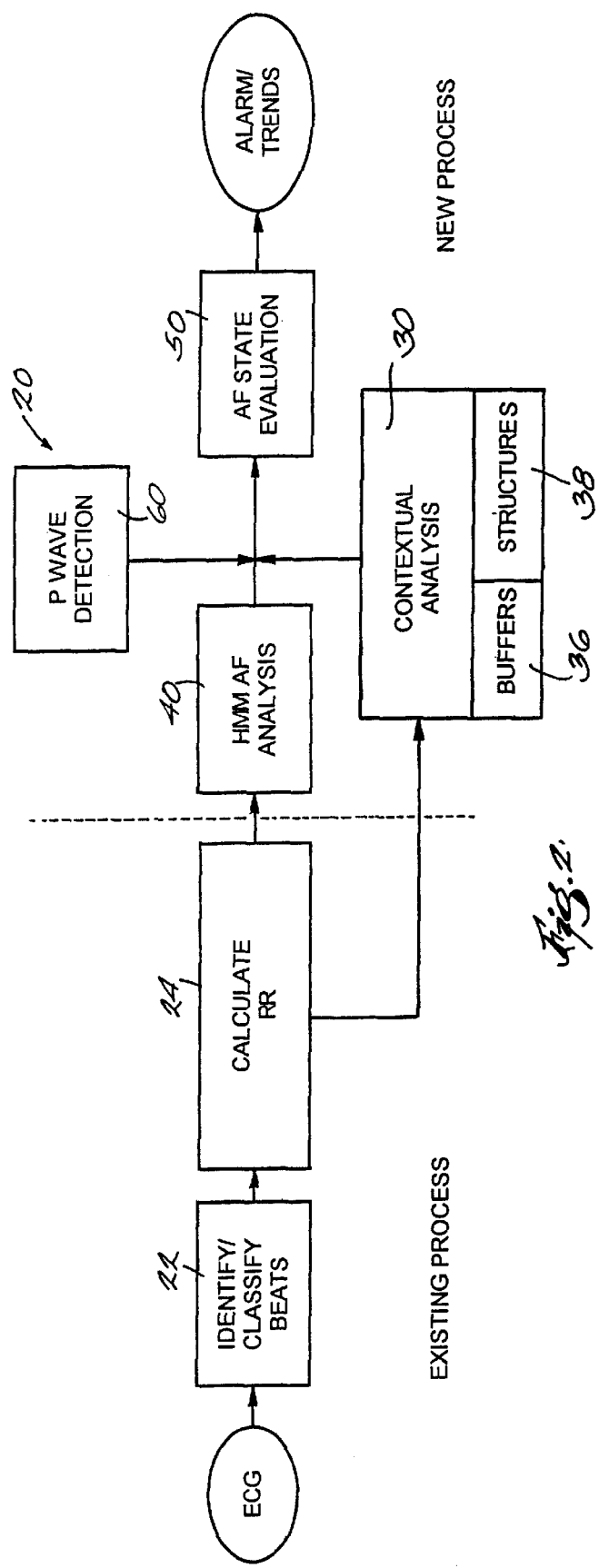
FIG. 2 is a schematic diagram of a system embodying the invention.

A system 20 embodying the invention is shown in FIG. 2. As should be apparent to those of ordinary skill in the art, the invention is intended to be implemented in software running on a computer or similar device capable of executing instructions and having such common hardware components as a central processor, memory, and input and output devices as well as software components such as an operating system and graphical interface, which of course can be incorporated in the operating system (all not shown). The components described herein are preferably software modules, which exchange information using parameters, function calls, and returns. However, equivalents could be created using hard-wired circuits.

The present invention was created as a result of improving and advancing a product known as the Monitoring EKpro Arrhythmia Detection software, which as mentioned above is available from the assignee of the present invention. As such, one embodiment of the invention relates to a module that detects AF and that is designed to be used with the EKpro software. Yet, the principles used in the invention are not limited to such an embodiment and neither are they limited to the detection of AF. The invention could be used to analyze other physiological waveform data such as pressure pulses.

When used as a companion to the EKpro product, the software of the invention can be included or excluded during configuration by setting a compile switch. In the example described, the switch is ATRIAL_FIBRILLATION_DETECTION (which could be included in a header file). To include the software module embodying the invention the compile switch is set to 1 and other configuration values (for various modules that will be discussed) should be set according to the application at hand. Table 1 lists the configuration values used in the invention and recommended default values that are based on the performance of the EKpro product. The default values can be adjusted to tune for variable performance in the AF detection, based on particular applications.

TABLE 1

| Configuration Value | Description | Default Value(s) |
|---|---|---|
| ATRIAL_FIBRILLATION_DETECTION | Compile switch used to include or exclude AF detection processing in EKpro | 1 |
| FLTLENGTH | Low pass filter length used in the HMM analysis | 32 |
| HMM0 through HMM6 and HMMUNK | HMM classifications used in the HMM analysis | 0–7 |
| NORMCODE, FUSCODE | Beat classification codes used by the state evaluation function | 15, 11 |
| PWAVE_THRESH | P wave detection threshold used to determine if a P wave is present. | 9 |
| NUMBER_RRS | Number of RR structures filled with RR interval history information. | 6 |
| RRBUFSZ | Buffer size of RR intervals used in contextual analysis. | 10 |
| NUM_SIMILAR_VALUES | Number of RR intervals from the RR buffer that are used to compare with the similarity index. | 7 |
| SIMILARITY_INDEX | Value used to compare RR intervals in the RR buffer to determine amount of similarity | 3 |
| BLOCK_MAP0 through | Beat maps used to | Discussed |

TABLE 1-continued

| Configuration Value | Description | Default Value(s) |
|---|---|---|
| BLOCK_MAP4 | identify common block patterns. | below |
| MAX_BIT_DIFF | Maximum number of different bits during comparison of beat map with the block maps. | 2 |
| REFRACTORY_WAIT_TIME | Refractory period length in samples used to wait for AF alarm or cancel AF alarm. | 7200 |

The system 20 receives physiological information in the form of ECG information. (The ECG waveform 10 of FIG. 1 is a representative example of such information). ECG information is input to a classification module 22 where the beats are detected and correlated to templates based on morphology. A number of templates are retained for correlation and, therefore, represent a number of different morphologies (if they exist). The incoming beats are included in the correlating template to represent one particular morphology. During classification, a number of measurements are made on the beats and templates to classify them as normal sinus, ventricular, etc. Noise processing is also performed at this time. Classification information and detection times of all the beats are recorded and sent to interval calculator 24. The interval calculator 24 determines intervals between R waves and outputs an RR interval value. Once the interval calculator 24 has determined the RR interval value, the value is sent to a contextual analysis module 30 and the RR buffers 36 and structures 38. The buffers 36 and structures 38 are updated with the newly determined value. The RR buffers 36 are used for similarity testing and the RR structures 38 are used to keep a history of the last several beats for further processing (as discussed in greater detail below). Beats that are classified as normal sinus beats or "fusion" beats are passed on to a probability engine 40. As is known in the art, the determination of normal and fusion beats is based upon morphology, timing, and the frequency at which they occur. The probability engine 40 also receives 1) the RR interval value and 2) noise information in the form of a flag that indicates whether any particular interval may be invalid due to the presence of noise.

The probability engine 40 is preferably implemented using a HMM methodology. In simple terms, the probability engine 40 receives the beat classification data and RR interval value generated by modules 22 and 24 and calculates a probability that the current beat or rhythm is an AF arrhythmia. The probability engine 40 outputs a state variable indicating if AF is present. The state variable is delivered to a state evaluation module 50.

While the probability engine 40 determines the probability of an AF condition (or, in other words, characterizes the "irregularity" of the rhythm), a key element of the invention is that it uses several additional regularity checks to make a final determination. The contextual analysis module 30 looks at several contextual characteristics. First, the module 30 determines matches between a predefined group of block maps and the current rhythm's beat map. The module 30 also determines similarities between consecutive RR interval values. In addition, the module 30 uses classifications to check for sequences of matching classes. The contextual analysis module 30 produces a contextual output.

In addition, P wave detection is used to find morphology characteristics of the dominant beat type, which is performed in a P wave detection module 60. The P wave detection module 60 determines whether the current beat exhibits a detectable P wave, by looking for the presence of such a wave before the QRS complex. The P wave detection module generates a detection output.

The state evaluation module 50 uses the outputs of the probability analysis module 40, the contextual analysis module 30, and the P wave detection module 60 to determine whether an AF condition exists. If the state variable of the probability engine 40 indicates an AF condition and the P Wave detection and contextual analysis modules output negative results, then the state evaluation module 50 determines that an AF condition is present. As will be discussed in greater detail, a state buffer may be implemented such that an AF condition must be detected for a specified amount of time before an AF alarm enable output is generated by the module 50. Likewise, the buffer may be used before an AF alarm disable output is generated.

Figure 3:
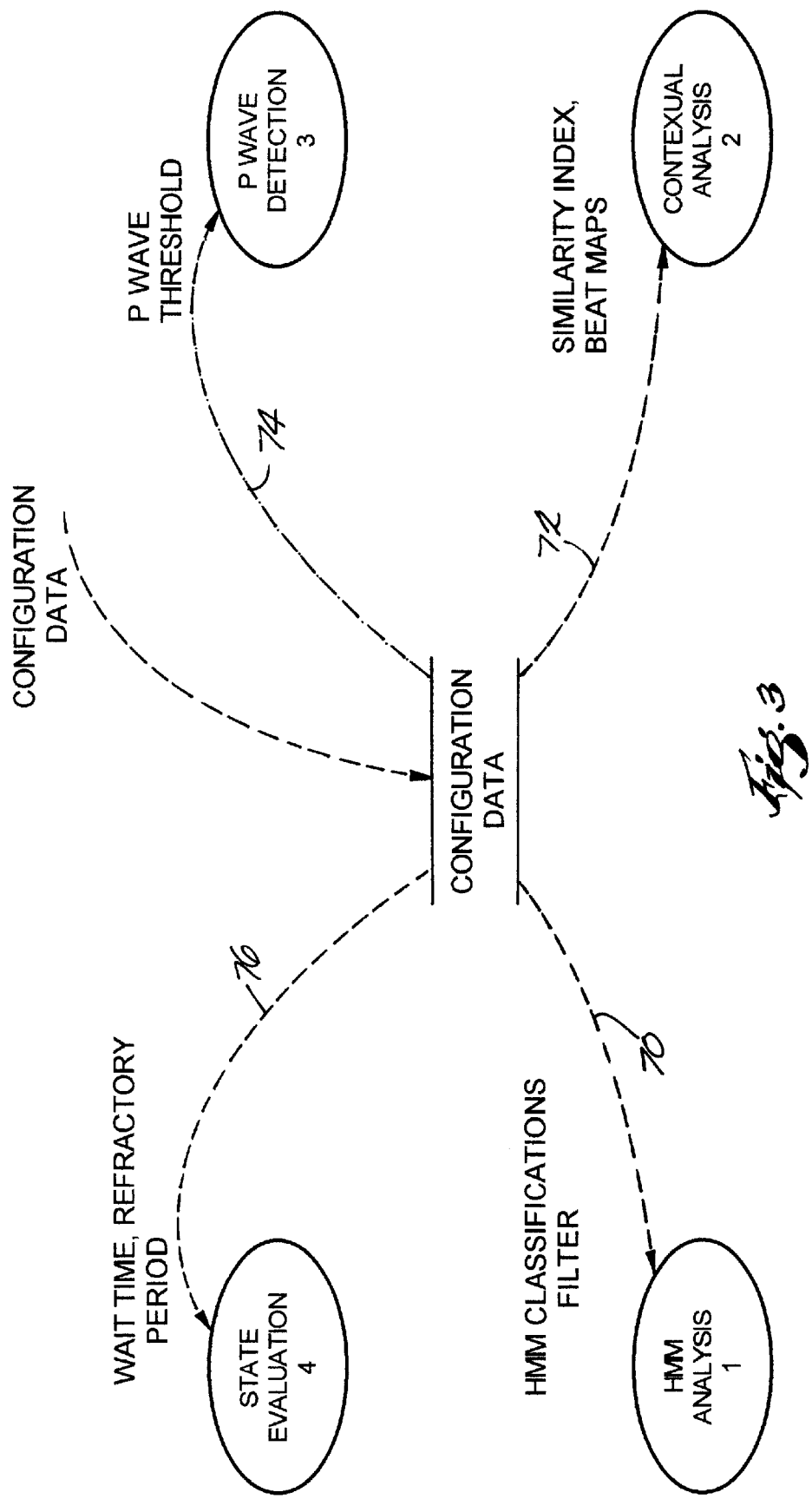
FIG. 3 is a top-level control flow diagram of processes used in the invention.
Figure 4:
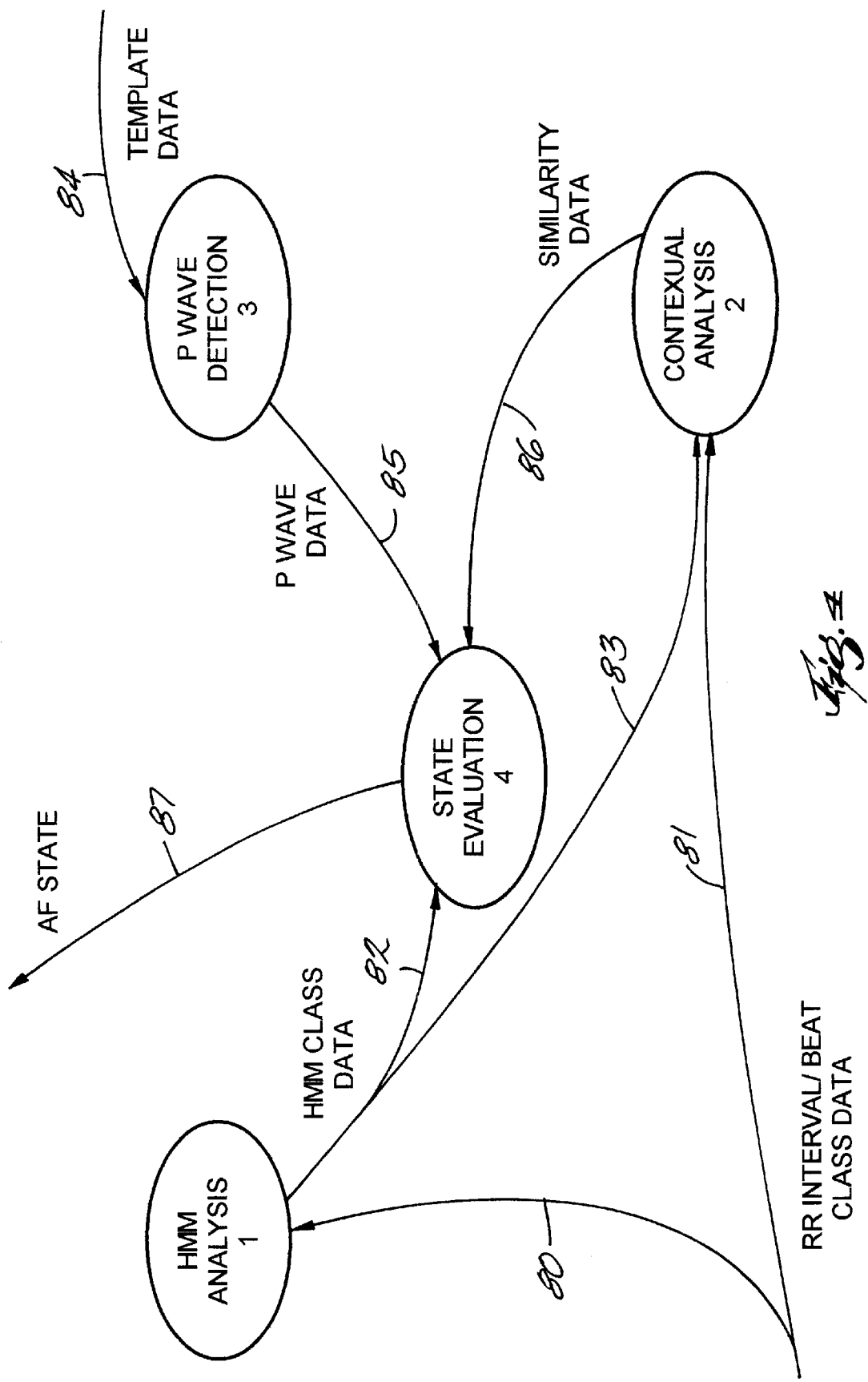
FIG. 4 is a top-level data flow diagram of processes used in the invention.

The control and data flow of the system 20 is illustrated in FIGS. 3 and 4. As noted above in the discussion of Table 1, the system 20 is preferably configured with particular configuration data. As shown in FIG. 3, the probability engine 40 is configured with certain HMM classifications (discussed below) and filter parameters, as shown by flow line 70. The contextual analysis module 30 is configured with similarity index information and beat maps (see flow line 72). The P wave detection module is configured with a P wave detection threshold (see flow line 74). Finally, the state evaluation module 50 is configured with a wait or buffer time and a refractory period (also discussed below) (see flow line 76). FIG. 4 illustrates the data flow among the four primary modules of the invention. As noted above, RR interval values and beat classification information are provided to both the probability engine 40 and the contextual analysis module 30 (see flow lines 80 and 81). A class-data-containing state variable from the probability engine 40 is provided to the contextual analysis module 30 and the state evaluation module 50 (see flow lines 82 and 83). Template data is provided to the P wave detection module 60 (flow line 84). The P wave detection module 60 provides detection information to the state evaluation module 50 (flow line 85). The contextual analysis module 30 provides similarity information to the state evaluation module 50 (flow line 86), which ultimately determines AF state and trend information that is delivered to a display or other output device (flow line 87).

Having discussed the overall operation and general architecture of the system 20, the individual components of the system will now be discussed in greater detail.

Figure 5:
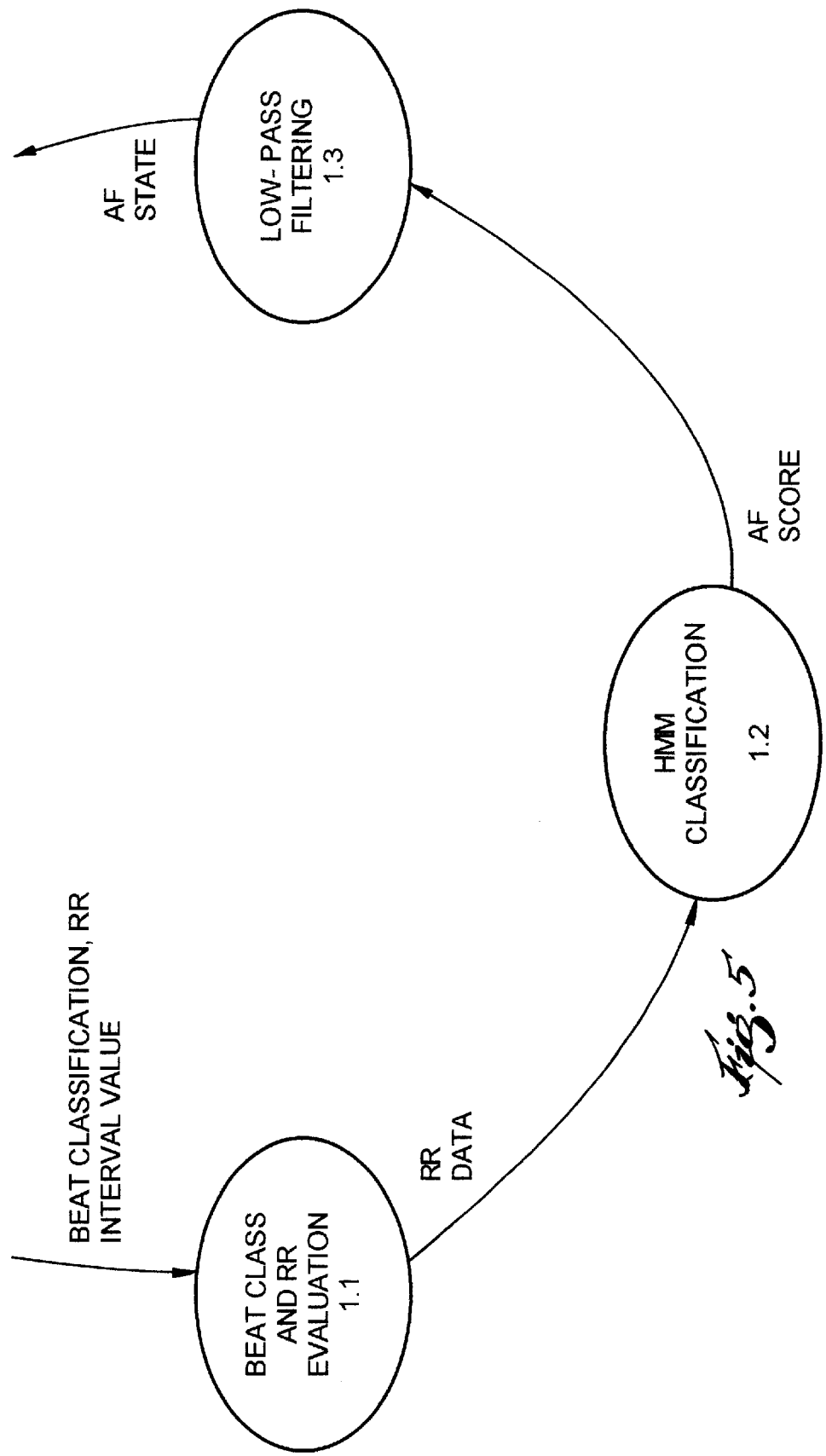
FIG. 5 is a data flow diagram of a HMM probability determination used in the invention.

The probability engine 40 analyzes the input RR interval values to determine an amount of "irregularity" in the ECG information being processed. The probability engine 40 outputs a state variable having one of two possible states: AF or NOT AF. The state variable is generated using a HMM lookup table. FIG. 5 shows the data flow associated with the processing carried out in the probability engine 40.

As is known, the HMM is a statistical model that uses observations to predict the state of a state machine. The observations are not direct observations of the state machine, but observations of external events, which provide indirect evidence of the model state. In the case of AF, the possible states are AF and NOT AF. The observations are sequences of RR intervals between normal beats.

In the present invention, the probabilities and model parameters of the probability engine 40 are designed using statistics from a training set of data. In the HMM used in the example described herein, the RR intervals are classified as one of seven possibilities. The classification uses prematurity ratio thresholds of 85% to 115%, as is shown in Table 2.

TABLE 2

| 0 | Undefined |
|---|---|
| <85% | Very Short (VS) |
| 85–90% | Short RR (S) |
| 90–95% | Slightly Short (SS) |
| 95–105% | Normal (N) |
| 105–110% | Slightly Long (SL) |
| 110–115% | Long (L) |
| >115% | Very Long (VL) |

Each RR interval value received by the probability engine 40 is compared to a running mean or average RR interval and assigned a HMM class based on prematurity. The running average is determined using the median of seven intervals: the last six intervals and one mean of these intervals. The sequences of three consecutive RR interval values describe a time pattern of the RR intervals and are used to determine or classify the current rhythm. The output of the probability engine 30 is generated for each RR interval value, based on the current RR interval value and two preceding RR interval values. In order to accomplish this, the probability engine 30 maintains six RR structures that contain the last six inputs from the beat classification module 22. The probability engine 30 processes the third RR structure each time it runs, then shifts the values in all the structures, pushing out the oldest value and making room for the newest value. This allows the probability engine to see the current interval as well as past and new intervals. The three-interval sequence provides a position in a HMM probability matrix or lookup table for finding an AF score. Depending on the implementation, the look-up table can be included in the file with the other functions or placed in accessible storage.

The look up table used in one embodiment of the invention was developed using an arrhythmia database, and is shown below in Table 3.

TABLE 3

| HMM = | [58 | 63 | 76 | 126 | 47 | 49 | 27 |
|---|---|---|---|---|---|---|---|
| | 135 | 66 | 55 | 134 | 107 | 55 | 32 |
| | 81 | 84 | 97 | 81 | 55 | 20 | 51 |
| | 92 | 153 | 160 | 130 | 125 | 130 | 75 |
| | 77 | 95 | 50 | 30 | 75 | 30 | 69 |
| | 43 | 75 | 77 | −22 | −30 | 26 | 33 |
| | −27 | 51 | 71 | 0 | −16 | 14 | 10 |
| | 89 | 80 | 90 | 150 | 77 | 45 | 76 |
| | 114 | 125 | 51 | 51 | 25 | 20 | 87 |
| | 45 | 60 | 19 | 81 | 84 | 15 | 64 |
| | 102 | 120 | 69 | 48 | 50 | 106 | 100 |
| | 100 | 90 | 35 | −23 | 42 | 77 | 100 |
| | 10 | 10 | 20 | 0 | −69 | 30 | 123 |
| | 19 | 40 | 60 | 47 | 19 | 54 | 53 |
| | 72 | 50 | 95 | 170 | 95 | 77 | 33 |
| | 134 | 69 | 42 | 125 | 45 | 90 | 120 |
| | 123 | 95 | 33 | −14 | 69 | 47 | 69 |
| | 62 | 47 | 5 | −53 | −23 | 60 | 125 |
| | 74 | 54 | −26 | −18 | 63 | 35 | 65 |
| | 69 | −5 | 100 | −12 | 30 | 35 | 90 |
| | 47 | 130 | 100 | 71 | 127 | 107 | 51 |
| | 46 | 97 | 95 | 90 | 38 | −47 | −11 |
| | 102 | 80 | 73 | 35 | −11 | −21 | 36 |
| | 35 | 79 | 0 | −53 | −26 | 2 | 67 |
| | −30 | −10 | −58 | −154 | −67 | 30 | 80 |
| | 51 | 39 | 24 | −60 | −44 | 60 | 105 |

TABLE 3-continued

| | 125 | 60 | 44 | 30 | 90 | 60 | 106 |
|---|---|---|---|---|---|---|---|
| | 96 | 79 | 160 | 110 | 140 | 97 | 57 |
| | 88 | 60 | 95 | 150 | 114 | 36 | 7 |
| | 77 | 90 | 47 | 72 | 65 | 30 | 77 |
| | 114 | 60 | 55 | −6 | −10 | −30 | 72 |
| | 17 | 33 | −10 | −79 | −20 | 62 | 113 |
| | 60 | 30 | 114 | −61 | 10 | 35 | 95 |
| | 60 | 25 | 15 | 17 | −25 | 9 | 25 |
| | 139 | 114 | 65 | 200 | 114 | 81 | 77 |
| | 44 | 35 | 69 | 120 | 54 | 45 | 10 |
| | 92 | 30 | 84 | 114 | 47 | 15 | 40 |
| | 65 | 45 | 30 | 33 | 0 | 20 | 50 |
| | 43 | 92 | 35 | −41 | 24 | 95 | 114 |
| | 20 | 10 | 30 | −45 | 5 | 0 | 104 |
| | 30 | 25 | 30 | 7 | −12 | −51 | 55 |
| | 66 | 60 | 117 | 125 | 60 | 74 | 38 |
| | 43 | 94 | 73 | 86 | 110 | 30 | −30 |
| | 93 | 117 | 95 | 141 | 75 | 20 | 30 |
| | 98 | 115 | 130 | 130 | 95 | 30 | 109 |
| | 107 | 123 | 127 | 4 | 60 | 55 | 93 |
| | 87 | 60 | 125 | 2 | 4 | 30 | 141 |
| | 25 | 75 | 65 | 22 | −50 | −36 | 77 |
| | 31 | 102 | 149 | 66 | 36 | −19 | −20]; |

In the present example, the analysis conducted by the probability engine 40 is based on the a posteriori probability of a given sequence of the RR interval values (X=[X(1), X(2), X(3), . . . X(n)]) with the initial state X(0) arising from a given rhythm model r. This probability is, according to the Markov hypothesis, given in Equation 1, where P(X(i)|X(i−1),r) is the probability for the transition from state X(i−1) to state X(i) for the rhythm model r.

$$P(X|r)=P(X(1)|X(0),r)*P(X(2)|X(1),r)* \ldots * P(X(N)|X(N-1),r) \qquad \text{Eqn. 1}$$

The rhythm model for AF detection is binary and, therefore, represents two states, AF and NOT AF. The transition matrix is determined based on these states and is defined in terms of the log of the transition probability ratios in Equation 2, where K is an arbitrary constant and S1 and S2 are one of the possible states, VS, S, SS, N, SL, L, VL.

$$TRMAT(S1|S2)=K* \log [P(S2|S1,AF)/P(S2|S1,NSR)] \qquad \text{Eqn. 2}$$

This means that a more positive table value indicates that the sequence has a higher probability of being AF, whereas a more negative value is indicative of a NOT AF state.

The values in Table 3 were found using data records from the Massachusetts Institute of Technology—Beth Israel Hospital (MIT-BIH) Arrhythmia Database. The "Gold" or truth AF annotations and RR intervals were used to obtain the total number of each sequence occurring during AF and NOT AF rhythms. The counts were then used to solve Equation 3 three-hundred and forty-three times, once for each sequence. The scaling factors were determined empirically to produce values that would be most appropriate for the present application.

$$HMM[(ix*49)+(iy*7)+iz]=100*\log_{10}(totalAFcounts[ix][iy][iz]/totalNSRcounts[ix][iy][iz]) \qquad \text{Eqn. 3}$$

When zero AF counts are detected for a certain sequence, the table value is determined using Equation 4. In the example described herein, the table values are limited to −200.

$$HMM[(ix*49)+(iy*7)+iz]=5* totalNSRcounts[ix][iy][iz] \qquad \text{Eqn. 4}$$

When there are zero counts of NOT AF for a certain sequence, the table value is determined using Equation 5. These table values are limited to +200.

$$HMM[(ix*49)+(iy*7)+iz]=5*totalAFcounts[ix][iy][iz] \qquad \text{Eqn. 5}$$

When a certain sequence is not represented in either AF or NOT AF rhythms, the table value is zero. As noted, Table 3 lists values used in the embodiment described.

Once an AF score or variable is generated using the look up table analysis discussed, the variable is low-pass filtered, preferably using a symmetrical finite impulse response ("FIR") filter that approximates exponential filter characteristics with a triangular response. The filter helps remove jitter and make the determination of AF onsets and offsets easier.

The initial state or output of probability engine 40 is NOT AF. The output of the filter is compared to two thresholds, an afThresh and a nsrThresh threshold, which were determined through performance testing. These values are set during execution of a function initalize_afi( ) during initialization in this embodiment, but can also be dynamically adjusted during analysis. If the output is greater than the AF threshold, then the state transitions to AF. It remains in that state until the output drops below the normal sinus rhythm (NSR) threshold, in which case the state transitions to NOT AF. The upper and lower thresholds provide a hysteresis control that keeps the system 20 from switching between the two states too quickly.

The contextual analysis module 30 finds similarity or patterns between the RR interval values being analyzed. While the probability engine 40 uses only three consecutive intervals, the contextual analysis module 30 uses many more intervals. In one embodiment, the contextual analysis module compares several 16-bit block maps to a running beat map of RR interval values. The contextual analysis module then looks at a buffer of RR interval values and determines a percent similarity between these intervals. If all the intervals are within the acceptable difference, then the rhythm is considered not irregular enough for AF. The contextual analysis module also looks for sequences of classifications from the probability engine that are normal. When one of these tests passes, a refractory or black-out period is put into effect and the AF state cannot transition from NOT AF to AF until the refractory period expires.

There are three major tests than can be carried out by the contextual analysis module 30. First, 16-bit beat maps are compared to the current rhythm. Each beat map represents a common beat pattern that may appear irregular, but is a result of a pathology other than AF. These types of maps are referred to as "block maps." In each map, the numeral 1 designates a "long" interval and a 0 designates a "short" interval. The long intervals are defined as probability engine classifications greater than three. The short intervals are defined as probability classifications less than or equal to four. A different sixteen-bit map represents the current rhythm and is retained and updated with every acceptable interval. This map is referred to as the beat map. The block maps are as follows:

| | |
|---|---|
| BLOCK_MAP0 0xaaaa | 0101010101010101 |
| BLOCK_MAP1 0x9249 | 1001001001001001 |
| BLOCK_MAP2 0x1111 | 0001000100010001 |
| BLOCK_MAP3 0x8421 | 1000010000100001 |
| BLOCK_MAP4 0x3333 | 0011001100110011 |

The beat map of the rhythm and each block map are compared with an exclusive OR operation to find the number of bits that are different between the two maps. If the bit difference is less than a maximum difference (such as MAX_BIT_DIFF), then the rhythm is considered to match the block map and the refractory or black-out period is enabled. If the bit difference is greater than the maximum difference, then the next set of tests is performed.

The contextual analysis module performs a percent similarity test to determine if the RR interval values are similar to each other in value or magnitude. An RR buffer is kept with the last RRBUFSZ intervals. Each time the test is performed, the buffer is sorted from least to greatest, in RR interval value, such as: $[X_1\ X_2\ X_3\ X_4\ X_5\ X_6\ X_7\ X_8\ X_9\ X_{10}\ \ldots\ X_{RRBUFSZ}]$ (a sorted RR buffer). As shown below, the difference between the first values in the buffer ($X_1$) and NUM_SIMILAR_VALUES is computed and compared to a percent similarity.

$(XNUM\_SIMILAR\_VALUES\_-X_1)?<(XNUM\_SIMILAR\_VALUES>>SIMILARITY\_INDEX)$ $(XNUM\_SIMILAR\_VALUES+1-X_{1+1})?<(XNUM\_SIMILAR\_VALUES+1>>SIMILARITY\_INDEX)$ $(XNUM\_SIMILAR\_VALUES+N-X_{1+N})?<(XNUM\_SIMILAR\_VALUE\ S+N>>SIMILARITY\_INDEX)$

The comparison continues until the comparison statement is true or the NUM_SIMILAR_VALUES+N=RRBUFSZ. When one of the statements in the comparison is true, the intervals are considered similar and the refractory period is enabled. If all comparisons are made and none are true, then one final test is performed. In this test the last four HMM classifications for the probability engine 40 are analyzed. If the last four HMM classifications are all normal intervals, then the refractory period is enabled.

The P wave detection module 60 performs an analysis of the atrial signal or signal portion of the ECG. During AF, the P wave is not present in the ECG signal. The signal preceding the QRS is measured to determine if P waves are present in the rhythm.

Figure 6:
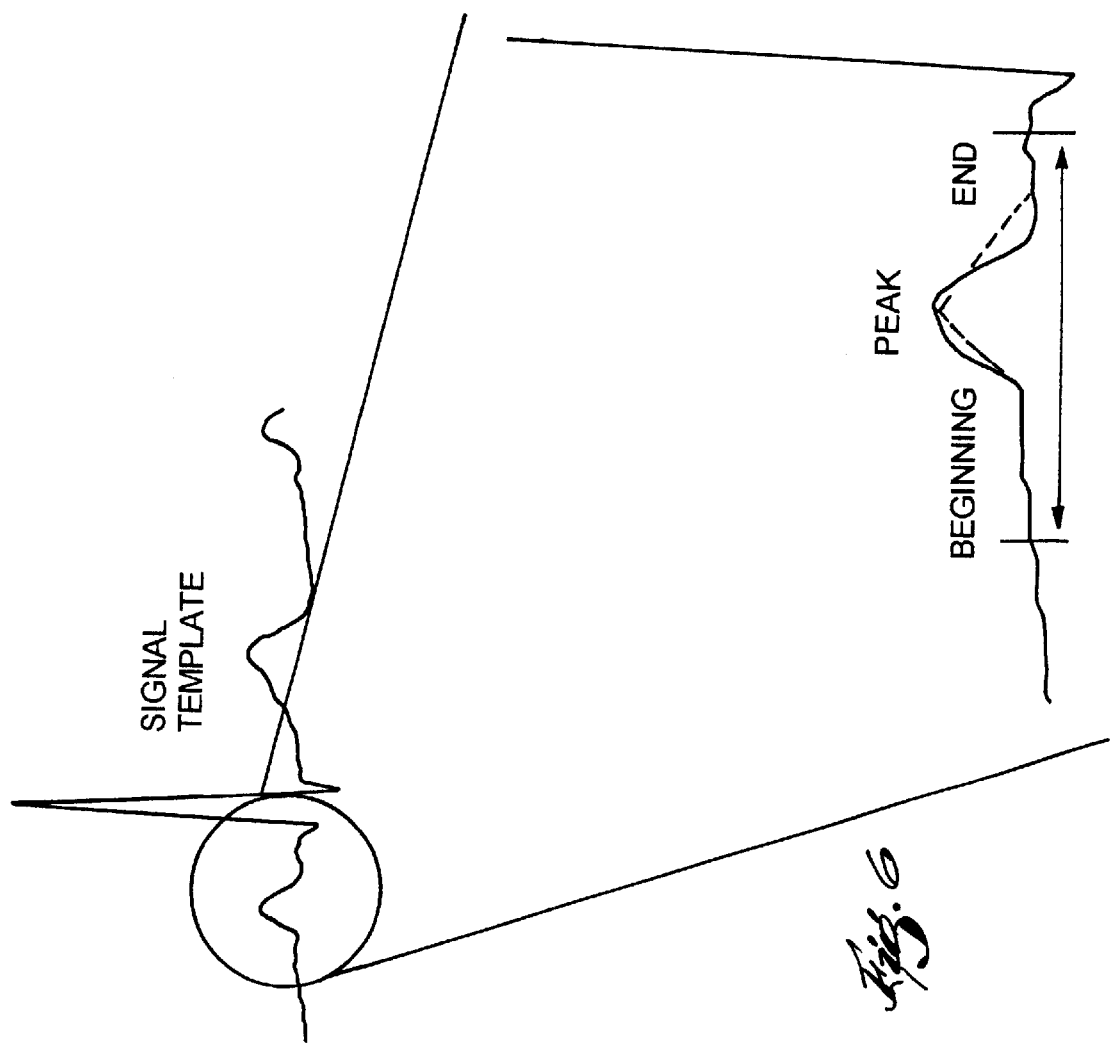
FIG. 6 is an illustration of P wave detection as implemented in the invention.

Each time an incoming beat matches a "favorite" template, the template is incrementally updated. Every sixteenth update, the template is measured for the presence of P waves. First, the detection window is defined. Then the signal extreme, or P wave peak, is found in the search window. Next the sixth differences of the waveform are calculated on the signal. This is accomplished by calculating the absolute difference between values separated by six data points (sixth difference=$|Value_n-Value_{n+5}|$, incrementing n until n+5 equals the length of the detection window). The maximum sixth difference before the peak marks the wave beginning at $Value_n$ and the maximum sixth difference after the peak marks the wave end at $Value_{n+5}$. Finally, the magnitude of the wave deflections, peak value minus beginning value and peak value minus end value, are compared to PWAVE_THRESH. If one deflection is greater than the threshold and the other deflection is at least half the threshold, then the wave is considered a P wave. An example of the results of this technique is shown in FIG. 6.

As noted above, the outputs of the probablility engine 40, the P wave detection module 60, and the contextual analysis module 30 are input to the state evaluation module 50. The state evaluation module 50 controls three state conditions. The conditions are no state change, and transitions from AF to NOT AF and NOT AF to AF. If the current state is AF and the probability engine 40 output indicates an AF condition, then there is no further analysis. Similarly, if the current state is NOT AF and the probability engine 40 outputs a NOT AF indication, then there is no further analysis and the current state remains the same.

The state evaluation module 50 maintains a one-minute history of current condition or state. The history includes twelve, five-second windows. Each window represents the current state of AF at that time and is continuously updated every five seconds. If the current state is AF and the probability engine 40 output indicates NOT AF, the history is updated to indicate NOT AF, but the current state is not changed. Once the history indicates that there has been thirty seconds (the most recent six five-second windows indicate NOT AF) of a NOT AF condition, then the current state is changed to NOT AF.

If the current state is NOT AF and the probability engine 40 outputs an AF indication, several checks are performed. If a P wave is detected, then the current state remains NOT AF. If the refractory period has been enabled from interval similarity or rhythm patterns, then the current state remains NOT AF. If both of these checks are negative, the history is reviewed to check for thirty seconds of an AF condition. If an AF condition is not present for thirty seconds, then the history is updated with AF, but the current state remains NOT AF. The state changes that occur in the state evaluation module 50 are set out in Table 4.

TABLE 4

| Current State | Probability Engine Output | Resulting processing |
| --- | --- | --- |
| AF | AF | No further processing |
| AF | NOT AF | Check for 30 secs of NOT AF Update history with NOT AF Change current state only when history indicates 30 seconds of NOT AF |
| NOT AF | NOT AF | No further processing |
| NOT AF | AF | If P wave detected, current state remains same If refractory period is enabled, current state remains same If first two tests fail, update history with AF Change current state only when history indicates 30 seconds of AF |

As noted, the outputs of the system 20 are a state variable, which indicates the alarm state of AF and a minute-by-minute trend variable of the state of AF. The output trend value indicates, for the current minute, if the patient is in AF. This is calculated by summing up the number of five-second time intervals in the one minute AF history and determining if the total time is greater than thirty seconds. When there is more than thirty seconds of AF in a minute, then the trend variable is positive, if not, then the trend variable is zero for that minute. FIG. 7 demonstrates how a trend may be displayed. FIG. 7 illustrates an ECG waveform 150. Those portions of the waveform during which an AF condition exists are marked with horizontal bars 152, 154, and 156, respectively. The periods of AF that occur may be summed to provide a total AF time 158. Of course, trending data could be displayed in other ways, such as bar graphs and the like.

As can be seen from the above, the invention provides an improved method and system of detecting arrhythmia. Various features and advantages of the invention are set forth in the following claims.

What is claimed is:

1. An arrhythmia detection apparatus comprising:
    a beat classification module having an input to receive ECG information;
    an interval calculator coupled to the beat classification module and operable to calculate an interval between recurring events;
    a probability engine coupled to the interval calculator and operable to output a state variable;
    a contextual analysis module coupled to the interval calculator and operable to match predefined maps to a current beat map and to generate a contextual output;
    a P wave detection module coupled to the beat classification module and operable to produce a detection output; and
    a state evaluation module coupled to the probability engine, the contextual analysis module, and the P wave detection module and operable to determine an arrhythmia condition based on the state variable, the contextual output, and the detection output.

2. An apparatus as claimed in claim 1, wherein the interval calculated by the interval calculator is an interval between successive R waves.

3. An apparatus as claimed in claim 1, wherein the probability engine implements an HMM analysis.

4. An apparatus as claimed in claim 3, wherein the probability engine is operable to classify intervals between recurring events using prematurity ratio thresholds.

5. An apparatus as claimed in claim 1, wherein the P wave detection module implements a sixth difference analysis.

6. An apparatus as claimed in claim 1, wherein the state evaluation module is operable to generate output in the form of alarm information.

7. An apparatus as claimed in claim 6, wherein the state evaluation module delays the output of alarm information until an alarm condition has existed for a predetermined amount of time.

8. An apparatus as claimed in claim 6, wherein the state evaluation module is operable to generate output in the form of trend information.

9. An apparatus as claimed in claim 1, wherein the contextual analysis module includes a buffer of interval values.

10. An apparatus as claimed in claim 9, wherein the contextual analysis module generates the contextual output based on a percentage of similarity of the intervals.

11. A method of detecting an arrhythmia from ECG information, the method comprising:
    classifying the ECG information;
    determining intervals between recurring events in the ECG information;
    determining a probability that an irregular condition exists based on classifying the ECG information and determining an interval between recurring events;
    generating a state variable based upon the determined probability;
    generating a contextual output based on similarities in intervals between recurring events;
    determining the presence of a P wave in the ECG information;
    generating a detection output based on determining the presence of a P wave; and
    determining the existence of the irregular condition based on the state variable, the contextual output, and the detection output.

12. A method as claimed in claim 11, wherein classifying ECG information includes detecting and correlating beats based on morphology.

13. A method as claimed in claim 11, wherein generating a state variable based upon the determined probability includes using a lookup table.

14. A method as claimed in claim 11, wherein determining a probability that an irregular condition exists includes maintaining a plurality of structures.

15. A method as claimed in claim 11, wherein generating a contextual output includes matching predefined maps to a current map of the ECG information.

16. A method as claimed in claim 11, wherein generating a contextual output includes performing a percent similarity test.

17. A method as claimed in claim 11, wherein determining the presence of a P wave includes calculating sixth differences of the ECG information.

18. A physiological condition detection apparatus comprising:
- a classification module having an input to receive physiological information;
- an interval calculator coupled to the classification module and operable to calculate intervals between recurring events;
- a probability engine coupled to the interval calculator and operable to output a state variable;
- a contextual analysis module coupled to the interval calculator and operable to generate a contextual output based on the classification of the physiological information and the intervals between recurring events;
- a wave detection module coupled to the classification module and operable to produce a detection output; and
- a state evaluation module coupled to the probability engine, the contextual analysis module, and the wave detection module and operable to determine a physiological condition based on the state variable, the contextual output, and the detection output.

19. An apparatus as claimed in claim 18, wherein the interval calculated by the interval calculator is an interval between successive waves.

20. An apparatus as claimed in claim 18, wherein the probability engine implements an HMM analysis.

21. An apparatus as claimed in claim 20, wherein the probability engine is operable to classify intervals between recurring events using prematurity ratio thresholds.

22. An apparatus as claimed in claim 18, wherein the wave detection module implements a sixth difference analysis.

23. An apparatus as claimed in claim 18, wherein the state evaluation module is operable to generate output in the form of alarm information.

24. An apparatus as claimed in claim 23, wherein the state evaluation module delays the output of alarm information until an alarm condition has existed for a predetermined amount of time.

25. An apparatus as claimed in claim 23, wherein the state evaluation module is operable to generate output in the form of trend information.

26. An apparatus as claimed in claim 18, wherein the contextual analysis module includes a buffer of interval values.

27. An apparatus as claimed in claim 26, wherein the contextual analysis module generates the contextual output based on a percentage of similarity of the intervals.

28. A method of analyzing physiological information, the method comprising:
- classifying the physiological information;
- determining intervals between recurring events in the physiological information;
- determining a probability that an irregular condition exists based on classifying the physiological information and determining an interval between recurring events;
- generating a state variable based upon the determined probability;
- generating a contextual output based on similarities in intervals between recurring events;
- determining the presence of a predetermined wave in the physiological information;
- generating a detection output based on determining the presence of a predetermined wave; and
- determining the existence of the irregular condition based on the state variable, the contextual output, and the detection output.

29. A method as claimed in claim 28, wherein classifying the physiological information includes detecting and correlating beats based on morphology.

30. A method as claimed in claim 28, wherein generating a state variable based upon the determined probability includes using a lookup table.

31. A method as claimed in claim 28, wherein determining a probability that an irregular condition exists includes maintaining a plurality of structures.

32. A method as claimed in claim 28, wherein generating a contextual output includes matching predefined maps to a current map of the physiological information.

33. A method as claimed in claim 28, wherein generating a contextual output includes performing a percent similarity test.

34. A method as claimed in claim 28, wherein determining the presence of a predetermined wave includes calculating sixth differences of the physiological information.

* * * * *